US006570657B1

(12) United States Patent
Hoppe et al.

(10) Patent No.: US 6,570,657 B1
(45) Date of Patent: May 27, 2003

(54) ARRANGEMENT FOR SURFACE PLASMON RESONANCE SPECTROSCOPY

(75) Inventors: Lutz Hoppe, Jena (DE); Peter Pfeifer, Jena (DE); Günter Schwotzer, Dorndorf-Steudnitz (DE)

(73) Assignees: Institut Fuer Physikalische Hochtechnolgolie e.V., Jena (DE); ANALYTIK Jena GmbH Analysenmessgeraete und Laboreinrichtungen, Jena (DE)

( * ) Notice: Subject to any disclaimer, the term of this patent is extended or adjusted under 35 U.S.C. 154(b) by 0 days.

(21) Appl. No.: 09/600,669

(22) PCT Filed: Apr. 6, 1999

(86) PCT No.: PCT/EP99/02353
§ 371 (c)(1),
(2), (4) Date: Jul. 20, 2000

(87) PCT Pub. No.: WO00/22419
PCT Pub. Date: Apr. 20, 2000

(30) Foreign Application Priority Data

Apr. 2, 1998 (DE) .......................... 198 14 811

(51) Int. Cl.[7] ............................................. G01N 21/55
(52) U.S. Cl. ..................................................... 356/445
(58) Field of Search ........................................ 356/445

(56) References Cited

U.S. PATENT DOCUMENTS

| 5,313,264 | A | | 5/1994 | Ivarsson et al. | |
|---|---|---|---|---|---|
| 5,485,277 | A | * | 1/1996 | Foster | ........................ 356/445 |
| 5,491,556 | A | | 2/1996 | Stewart et al. | |
| 5,917,607 | A | * | 6/1999 | Naya | ........................... 356/445 |
| 6,239,876 | B1 | * | 5/2001 | Brandenberg | ................ 356/451 |

FOREIGN PATENT DOCUMENTS

| DE | 19615366 | 10/1997 |
|---|---|---|
| DE | 19732619 | 2/1999 |
| EP | 0286195 | 10/1988 |
| WO | WO 93/25909 | 12/1993 |
| WO | WO 95/22754 | 8/1995 |
| WO | WO 97/40366 | 10/1997 |

OTHER PUBLICATIONS

Biosensors & Bioelectronics 9 (1994) pp. 139–146. "Characterization of biomembranes by spectral ellipsometry, surface plasmon resonance and interferometry with regard to biosensor application" by Ch. Striebel et al.

(List continued on next page.)

Primary Examiner—Richard A. Rosenberger
(74) Attorney, Agent, or Firm—Jordan and Hamburg LLP

(57) ABSTRACT

Surface plasmon resonance spectroscopy device includes an optical prism with a sample cell associated therewith and at least two sample detection areas that are provided with a thin metal coating selected for implementation of the SPR method and which contains, at least partially, surface-immobilized areas. Light is conducted via an optic fiber, collimated by a collimator with an aperture to a base surface of the prism, applied to an entrance of the optical prism. A multi adaptable diaphragm is provided between the collimator and the entrance surface. The diaphragm defines a path to the prism in a chronologically successive manner. Switching states are allocated to spectra corresponding to the switching states, whereby the spectra are obtained by detecting the light that leaves the prism through another collimator connected to another optic fiber applied to a polychromator wherein spectrally decomposed light is detected and evaluated by an evaluation and control unit.

20 Claims, 4 Drawing Sheets

OTHER PUBLICATIONS

Figure 1:
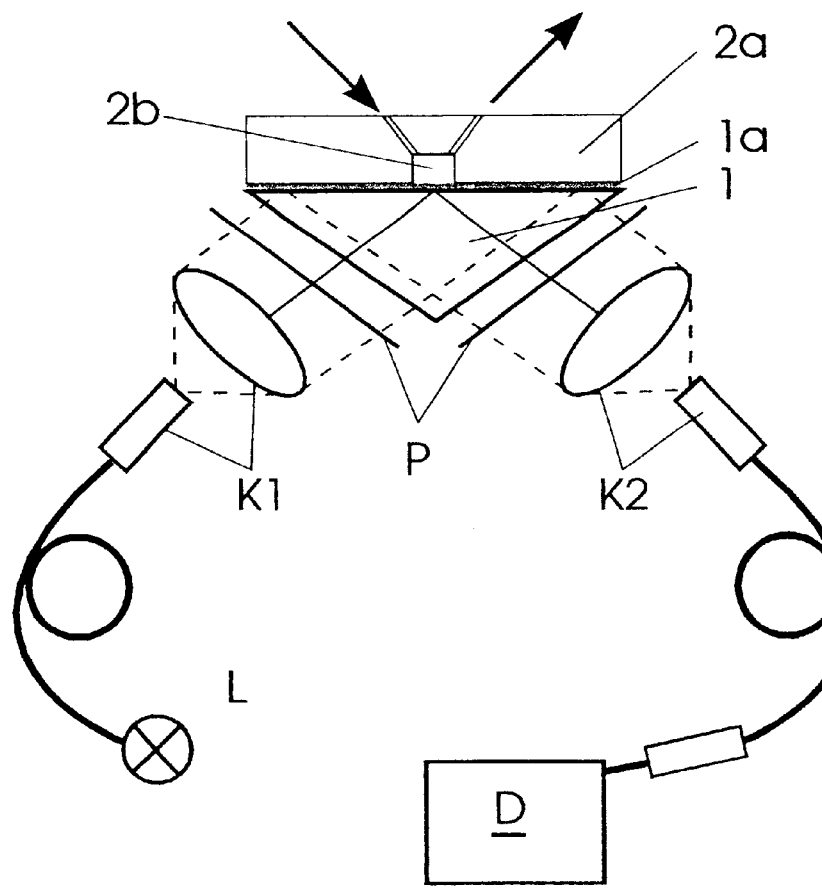

Anal. Chem. 1998, 70, pp. 703–706. "Surface Plasmon Resonance Multisensing" Charles E.H. Berger et al.

Sensors and Actuators B 24–25 (1995) pp. 756–761. "Near–infrared surface plasmon resonance in silicon–based sensor: new opportunities in sensitive detection of biomolecules from aqueous solutions by applying microstep for discriminating specific and non–specific binding" by Gunnar Brink et al.

Biacore AB, Rapsgatan 7, S–75450 Uppsala, Sweden 1996.

* cited by examiner

ARRANGEMENT FOR SURFACE PLASMON RESONANCE SPECTROSCOPY

BACKGROUND OF THE INVENTION

The invention relates to an arrangement for surface plasmon resonance spectroscopy, which in particular can be used for a direct analysis of the interaction between bio-molecules and which permits a multi-component analysis.

There is known a very sensitive method for specifying the characteristics of boundary faces that, in the references, is referred to as surface plasmon resonance spectroscopy, generally designated as SPR (surface plasmon resonance). This method is based upon the optical excitation of surface plasmons in thin metal layers. The resonance conditions for the excitation of surface plasmons strongly depend on the optical properties of the dielectrics surrounding the metal layer. Hence, it is principally feasible to determine the refractive index and the layer thickness of thin dielectric layers with high precision.

SPR-spectroscopy finds an increasing application in the biochemical analysis, since it permits a direct analysis of the interactions between the bio-molecules (for example, antibody/antigen reactions). To this end a reactant (ligand) is immobilized on the metal surface, the other reactant (analyt) is passed over the surface in solution. The interaction can be directly detected as an increase in layer thickness; there is no marking of the reactants necessary as, for example, with the radioimmunoassay (RIA) or the enzym-linked immunosorbent assay (ELISA). These and further methods of the prior art have been described in detail by Striebel, Ch.; Brecht, A.; Gauglitz, G. in Biosensors & Bioelectronics 9 (1994), 139–146. Nearest to the present invention comes the SPR-method, described therein, in which light originating from a light conducting fiber is directed via a collimator and an optical polarizer upon an optical prism, on the base of which a thin silver coat enabling SPR is deposited that is covered by a chip, which is provided with a sample flow channel extending perpendicularly to the illumination propagation direction. The light that is reflected at and affected by the silver coat in response to the respective surface coverage, is then directed to a diode array spectrometer via a light conducting fiber. A simultaneous multi-component analysis is not possible with the arrangement described therein, because there can only be provided one optical and one fluid channel. In WO 97/40366 an arrangement is described, in which the detection of a plurality of samples arranged on a substrate sheet is realized in that the beams reflected on the samples are simultaneously imaged upon a matrix-shaped detector (CCD-matrix or video camera). All samples are successively illuminated with light of different wavelengths in order to determine the resonance wavelength. A tunable light source or a scanning monochromator is provided in the emitted path of rays for the selection of the wavelengths. Though the spectral measurement avoids the disadvantages of the intensity measurement described herein below, this system, however, can only be realized under considerable costs and only with comparatively large stationary devices, due to the required components.

Furthermore, arrangements of the prior art are known, which make use of the SPR method, but only provide for a pure angular detection of the totally reflected light. So a device is known from the product specification of the firm Biacore AB, Rapsgatan 7, S-75450 Uppsala, Sweden 1996, the setup of which in principle corresponds to the above described arrangement, whereby the illumination is provided by converging light beams and as a detecting element a diode array is directly and as a structural unit associated to the second lens system. Such a setup requires a comparatively large and mechanically bulky measuring head that can exclusively be employed in a stationary device. Furthermore, Berger, Ch. E. H. et al in "Surface plasmon resonance multisensing", Anal. Chem. 1998, 70, p. 703–706 describe an arrangement that permits a multi-channel measurement, which however is based upon an intensity measurement as a measuring principle, which is connected with the known disadvantages, namely the high requirements for a stability of the light source and of the detector elements that only can be obtained with considerable expenditures for a control system. Furthermore, the arrangement described therein limits the angular range otherwise basically available, in which plasmon resonance oscillations can be detected, since only a narrow angular range can actually be exploited by the measuring method described there. Moreover, the arrangement described there and which makes use of a video camera and of a video recording, has comparatively high expenditures for equipment, apart from the fact that a simultaneous multi-channel measurement is not provided for, since the measuring results can only be evaluated afterwards in time sequence.

A further arrangement belonging to that group of arrangements is described by Brink, G. et al, in "Near infrared surface plasmon resonance in silicon-based sensor", Sensors and Actuators B 24–25, 1995, p. 756–761. Therein a silicon wafer is used for the sample chip, the silicon wafer is provided with a step that is differently coated so that two resonant angular ranges and, hence, two channels can be detected, when the illumination spots covers both faces of the step. Even when using a plurality of steps therein, the number of exploitable channels would be principally limited by the angular range, in which the SPR method will work. Still more serious will be the disadvantage that with the different spectral position of the steps, the mutual sensitivity of the steps will not be identical.

Due to the problems mentioned, the commercially available SPR measuring technique has failed to find a wide application.

SUMMARY OF THE INVENTION

It is an object of the invention to provide a miniaturized arrangement for surface plasmon resonance spectroscopy that is designed as a cost-effective and portable unit and that is also adapted to perform a multi-component analysis, in particular for the interaction between bio-molecules.

In the frame of the invention, light originating from a broad-band light source and directed via a light conducting fiber to a collimator of a comparatively wide exit aperture is, by virtue of said collimator, directed upon an optical prism, at the base face of which a sample receiving cell is located, the bottom of which is provided with a thin metal layer enabling the SPR-method. It lies within the scope of the invention to also provide the base face of said prism with the metal layer mentioned or, by way of immersion, to deposit a metal coated substrate on the base face of the prism. The very essence of the invention consists in providing a multifold and in different positions switchable diaphragm between the collimator and the first prism entrance face, whereby in each switching state of the diaphragm definite ranges of the bottom of the sample cell are illuminated. The respectively affected and reflected light is fed, via a second collimator with connected light conducting fiber, into a polychromator, the spectral signals of which are captured by a CCD-array or by a diode array and passed on to an evaluation and control unit, in which a correlation is performed to both, the respective switching states of the diaphragm and to a signal obtained from a reference channel provided on the sample cell.

DETAILED DESCRIPTION OF THE INVENTION

Figure 2:
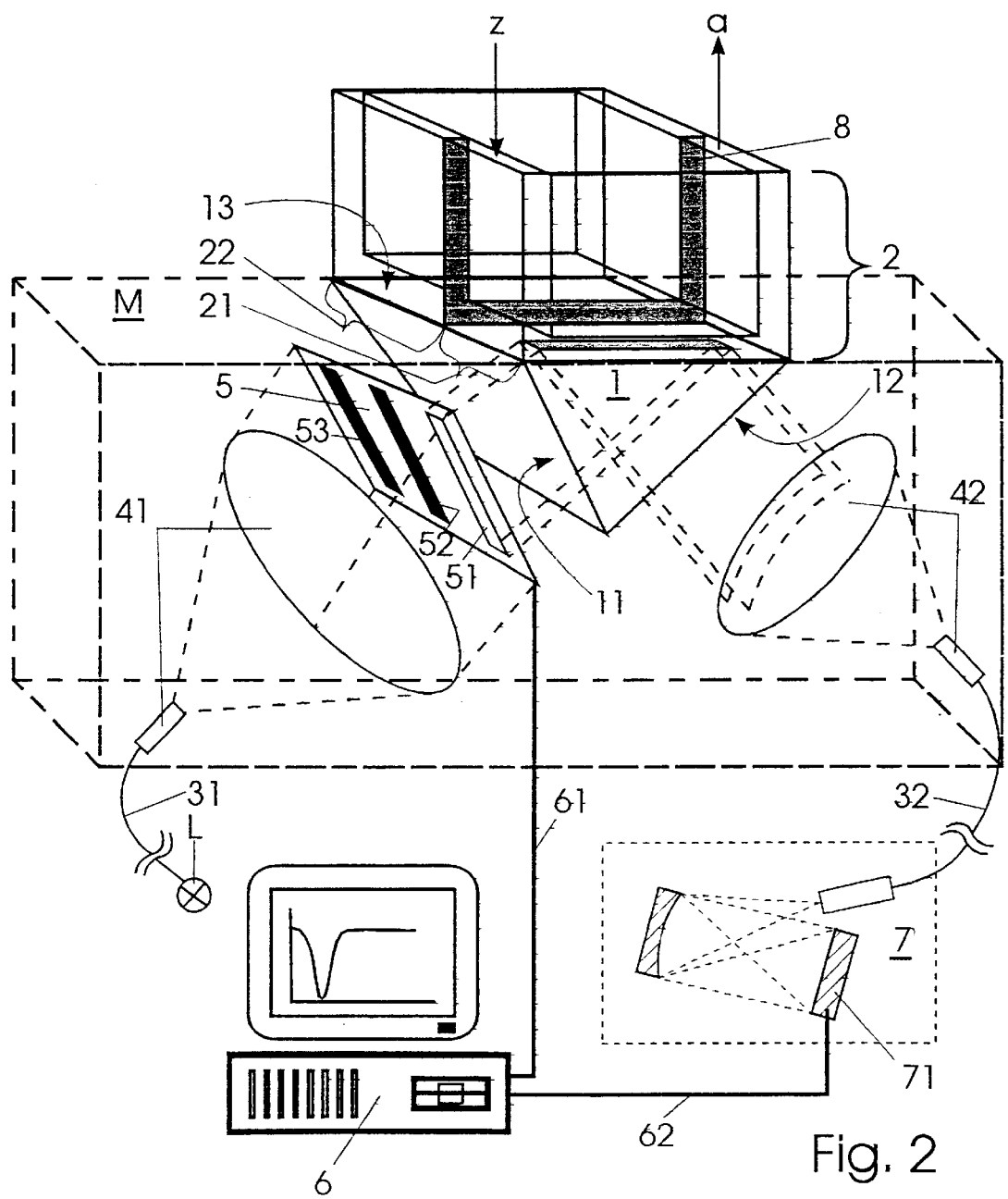
Figure 3A:
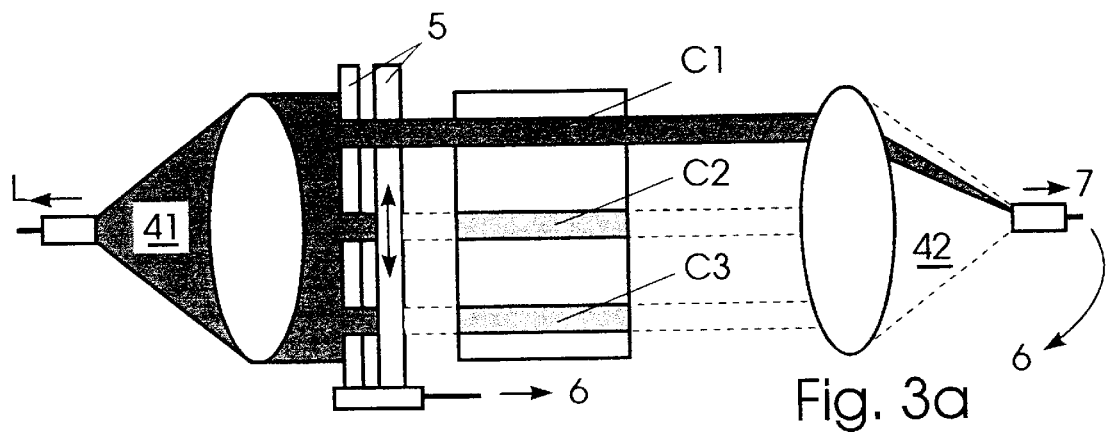
Figure 3B:
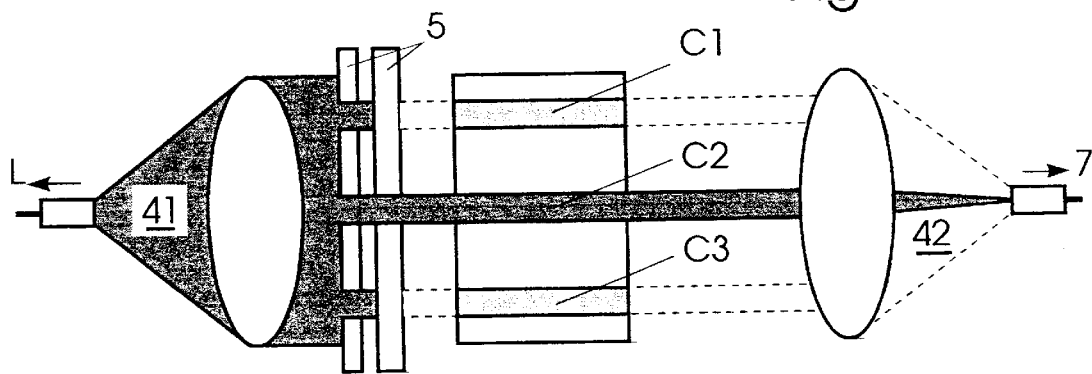
Figure 3D:
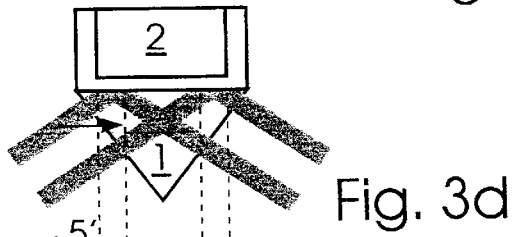
Figure 3C:
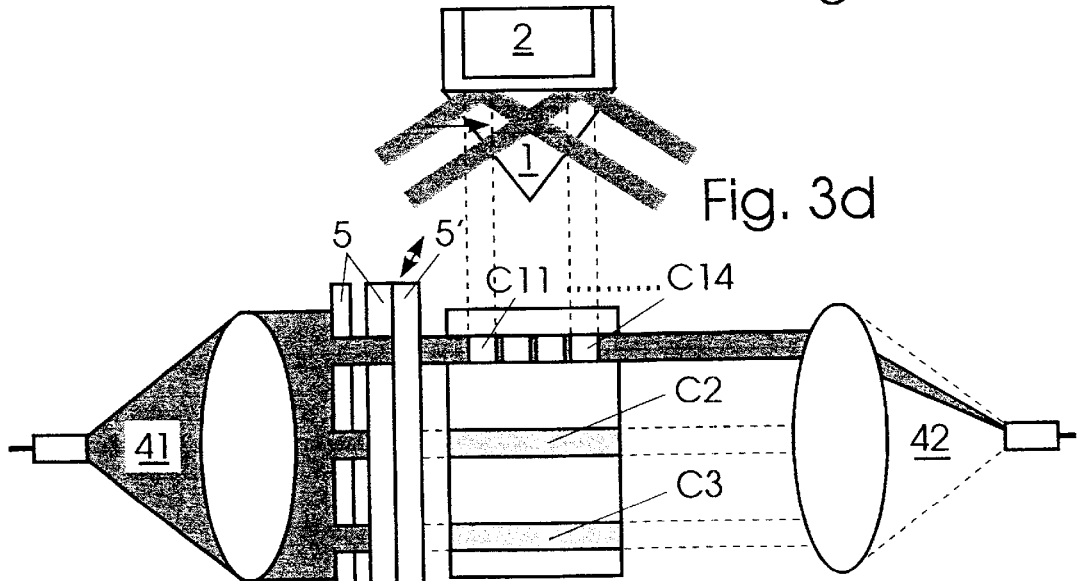
Figure 4:
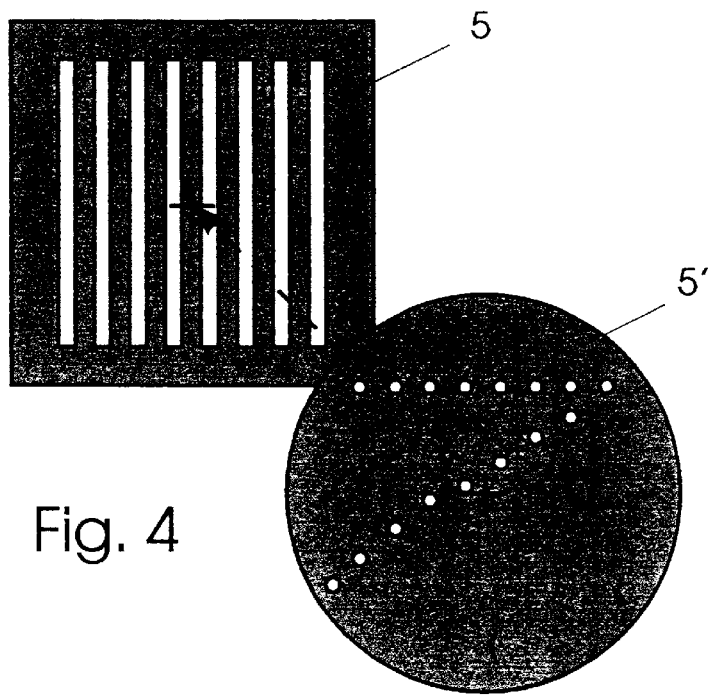
Figure 5:
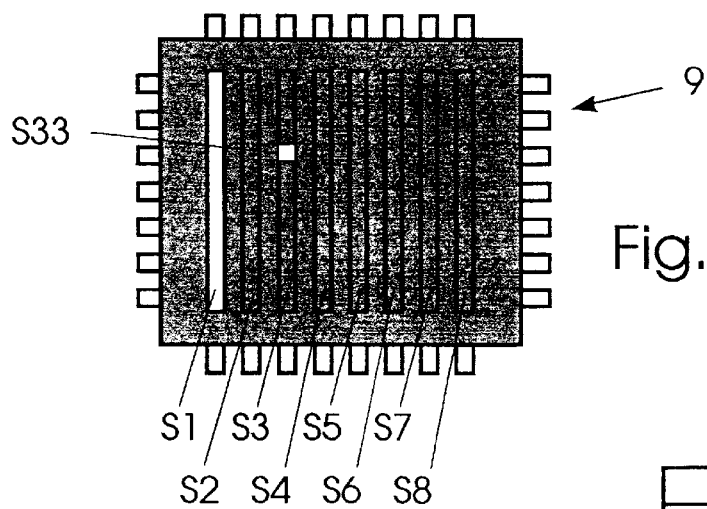
Figure 6:
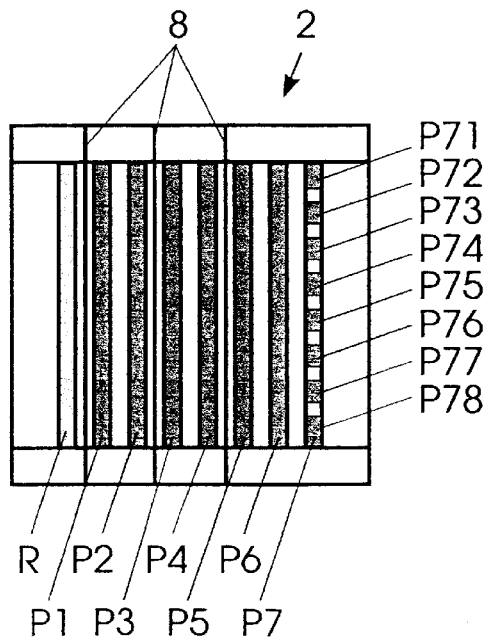

In the following, the invention will be explained in more detail by virtue of the schematical embodiments. There is shown in:

FIG. 1 an arrangement of an SPR measuring set-up according to the state of art,

FIG. 2 a more detailed representation of an SPR-arrangement according to the present invention and its essential units, partially in perspective view, FIGS. 3a to c a bottom view of FIG. 2, in which different paths of beams obtainable with the present invention are schematically shown, FIG. 3d a lateral view for clarifying two feasible paths of beams according to FIG. 3c in analogy to FIG. 2, FIG. 4 a principle mechanical design of an embodiment of the multifold switchable diaphragm, FIG. 5 a principle opto-electrical design of an embodiment of the multifold switchable diaphragm, and FIG. 6 exemplified, an embodiment of the sample cell and the bottom of the cell.

In FIG. 1 there is shown an arrangement of an SPR measuring set-up according to the prior art. Light from a light-source L is coupled into a light conducting fiber and, via a first collimator K1 directed onto an optical prism 1. A Teflon chip 2a is deposited on the prism 1, the Teflon chip comprising a flow chamber 2b, which is adapted to be passed by a sample fluid in the directions indicated by the arrows. The base range of the prism provided with a thin metal coat 1a, by which a ligand is immobilized. The light reflected on this area is spectrally and differently affected by the plasmon interactions depending on the degree of coverage of the immobilized layer with the analyt, and detected by a second collimator K2 and fed into a diode array spectrometer D. Due to the fact that plasmon oscillations can only be excited by definite polarization directions of the incident light, optical polarizers P are at least provided in one of the designated light paths according to FIG. 1. An excitation of the plasmon oscillations by a definite linear polarization direction is also necessary with the inventional solution described herein below, without the necessity to be referred to in more detail, since it is a measure well-known in the art. On the one hand, a substantially simultaneous multi-component analysis cannot be carried out with the arrangement described with reference to FIG. 1. On the other hand, problems occur with the practical use of these affinity sensors inasmuch as variations of the refractive index in the substances to be analyzed may occur due to thermal variations, which falsify the measuring signal. Furthermore and in spite of a high selectivity, in particular of biochemical reactions, non-specific bindings on the immobilized metal surface can lead to false measuring results.

In FIG. 2 there is shown, partially in perspective view, a more detailed representation of an SPR-arrangement according to the present invention with its essential units. In analogy to the prior art, light, here from a broad-band light source L, is coupled into a light conducting fiber 31, preferably a multi-mode light conducting fiber, passed into a collimator 41 and directed onto the entrance face 11 of the prism. A particularly advantageous embodiment of a sample cell consists of a sample cell 2, which is adapted to be positioned upon the base face of the prism and the inner bottom of which is provided with the thin metal layer mentioned. Other cell designs and, for example, the deposition of the mentioned thin metal layer on the base face of the prism, as common use with the prior art, can also be realized with the arrangement proposed herein. The light here reflected at the bottom of the sample cell 2 is received, via the exit face 12 of the prism, by a second collimator 42 and passed on, by a light conducting fiber 32, for being evaluated. In contrast to the prior art, the invention comprises at first a locally multifold switchable diaphragm 5, which in the example according to FIG. 2 is represented as a diaphragm with three switchable slits 51, 52, 53, whereby in FIG. 2 the slits 52, 53 are shut and the slit 51 is open. The respective switching states of the diaphragm 5 are fed into an evaluation and control unit 6 by virtue of conventional electronic units, not shown in detail, via a data and control line 61. Furthermore, the lateral extension of the single slits of the diaphragm 5 is so dimensioned that the their image substantially covers the base face 13 of the prism in one direction of extension, as indicated in FIG. 2 by the dark field projection area which is produced by the parallel light of the first slit 51. Furthermore in FIG. 2, two sample detection ranges 21, 22, which are separated and spaced from one another by a wall 8, are provided which are formed in the example in-between the double wall of the cell 2, whereby the arrow z designates the sample in-flow and the arrow a designates the sample outflow. The potentialities inherent in the exemplified separation are explained in more detail in FIGS. 3 and 6. The splitting up of the light transmitted from the light source L by way of the light conducting fiber 31 into the single measuring channels provided, shown in FIGS. 3 and 6 in more detail, is performed in the light beam which is collimated in the collimator 41 by means of the multifold switchable diaphragm 5.

In FIGS. 3a and 3b different paths of rays, which can be obtained with the present arrangement, are shown in a bottom view according to FIG. 2. In all embodiments shown, the selection of the single measuring channels takes place in a time sequence by a switchable diaphragm that can be of different design and that only passes on one respective light strip formed by the diaphragm. This light strip excites the SPR oscillations on the metal coated cell bottom in the associated measuring channel (refer to FIG. 3a, channel C1; FIG. 3b, channel C2). These SPR oscillations are then spectrally affected according to the, for example, biochemical interaction, and focussed onto the second light conducting fiber 32 by the collimator 42, and fed into the polychromator 7 for evaluation. The evaluation and control unit 6 ensures the correlation of the spectra succeeding in time to the measuring channels (time-division multiplexing). In FIG. 3c there is exemplarily outlined a further embodiment of the present arrangement, in which also a plurality of light strips can be sequentially imaged onto one channel by a suitable design of the diaphragm, in the example indicated only in the channels C1 by C11 . . . C14, so that a multi-component analysis can be carried out also in the shown direction by a different immobilization of the individual measuring areas. A diaphragm, which permits such an operation, is exemplified in FIG. 4, which consists here of a multi-slit diaphragm 5 and a rotatable multi-hole disk diaphragm 5, associated to the first one. Electro-mechanical or piezo-electric drive means for performing a defined and precise adjustment of such conceivable embodiments of diaphragms belong to the well-known prior art and need not be explained herein any further. Any desired modification of the required diaphragm principle for operating the present arrangement lie within the scope of the invention. Thus, a liquid crystal cell 9 can be used for the locally multifold switchable diaphragm 5, 5', whereby the liquid crystal cell is arranged between two polarizers, not shown in detail in FIG. 5. Such components (which compare to an LCD-display) are commercially available. Any desired diaphragm geometry matching the embodiment of the sample cell bottom can be realized by way of suitable electrode forms. At the same time, preferably linear polarized light for the excitation of the SPR is available at the exit of the diaphragm 9 with such an embodiment of the diaphragm. The serial switching of the single channels is carried out by applying a corresponding electric voltage across the transparent electrodes of the liquid crystal cell. In the example of FIG. 5, there is shown a totally open illumination slit S1 and a partial slit range S33, which is adapted to be opened after shutting the slit S1, and which is provided for illuminating a partial sample range Pxy (refer to FIG. 6). Since both, temperature variations are unavoidable when using the proposed arrangement, and unspecific bindings on the immobilized surfaces lead to falsifications of the measuring results, a measuring channel, which is selectable at will, is reserved as a reference channel in each of the represented embodiments, the use of which is described herein below. Said unspecific bindings cannot be entirely excluded at measurements of very complex matrices such as, for example, blood plasma or extracts from foodstuff. Depending on the measuring object and on the actual cell design, the reference channel can be designed in many forms. Thus, this reference channel according to FIG. 2 can be, for example, the sample detection range 21, which is separated from the proper measuring channels in the sample detection range 22 by the wall 8. Provided that there is not such a wall, the reference channel can also be formed by a not immobilized sample detection range, and the like. FIG. 6 indicates by example an embodiment of sample detection ranges P1 to P7, whereby the range P7 is again subdivided in subranges P71 to P78. At the same time, three walls 8 and one reference channel R are provided in this example. The actual design of the sample cell 2 and of the sample detection ranges exclusively depends on the respective object of application and on the operation site of the proposed arrangement. Thus, it is possible to design, for example, the replaceable sample cell 2 as a bypass that can be included, for example, in a flow-reactor. The great advantage of the proposed arrangement consists in the very small embodiment of the actual optical measuring head M, constituted of the prism 1, the collimators 41 and 42, as well as of the multifold switchable diaphragm, and can be used as a hand-held unit. The remaining units of the arrangement that are required for the control and evaluation can be stationed far away from the actual measuring site by a variably defined length of the light conducting fibers 31 and 32.

When in use, the proceeding according to the inventional arrangement is basically as follows: at first the spectral transmission function of the entire measuring system is recorded and stored in the evaluation and control unit 6. To this end and as one possibility, the entrance polarizer, not shown in detail, is initially rotated in such a way that linear polarized light is analyzed perpendicular to the plane of incidence. Hence, there is no excitation of surface plasmons possible. Another possibility consists in initially filling the sample cell 2 with air, so that there is again no excitation of surface plasmons given in the analyzed spectral range. In this way the transmission function of the system is gained. In the application used herein, the recording of the SPR spectra is carried out in liquid media. With an appropriate design of the measuring head M, the application of the arrangement is, however, not restricted to liquid media, a measurement can be taken in gaseous media in the same manner as well. These spectra are superimposed to the above mentioned transmission function. In order to obtain an SPR spectrum suitably calibrated for the evaluation, the SPR spectra, which are obtained in the polychromator 7, detected by a CCD-array or a diode array 71 and fed into the evaluation unit 6 via a data line 62, are computationally divided by the stored transmission function in the evaluation unit 6 after each single measurement. The determination of the searched for resonance wavelength, that is, the wavelength at which the light reflected at the boundary area of the sample detection area is a minimum, is obtained, for example, by fitting-on a polynomial of a preselectable grade and by determining the peak of this polynomial. In the evaluation and control unit 6 the corresponding detected spectra are associated to each instantaneous diaphragm position after the above described calibration. Depending on the measuring task and on the reaction kinetics, this operation can be repeated at will in order to detect the respective minima of the resonance spectra. In a possible example, the measuring channel and the reference channel shall be similarly immobilized. In the measuring channel, through a sample cell 2 separated by a wall 8 into two parts, a sample to be tested containing the substance to be identified is passed over the sample detection area. Simultaneously, in the reference channel, a similar reference sample without the substance to be identified is passed over the further sample detection area. In this way the signal variations in the reference channel due to unspecific bindings on the chip surface and due to refractive index variations as a result of temperature variations are detected in the same way as in the measuring channel. In the evaluation unit the signal variations in the reference channel are subtracted from the respective signal variations in the measuring channel, therefrom results only the measuring signal caused by the specific variations.

What is claimed is:

1. An arrangement for surface plasmon resonance spectroscopy (SPR), comprising:

an optical prism, a sample cell being associated to said prism, said sample cell having at least two sample detection ranges;

said arrangement being provided a thin metal layer adapted for the SPR method;

at least one of said sample detection ranges being designed as a surface immobilized sample detection range, a broad-band light source for emitting light, said light being directed via a light conducting fiber and through a collimator to an entrance face of said optical prism, said collimator having an aperture adapted to a base face of said prism, said collimator collimating said light, a locally switchable diaphragm, said diaphragm being between said collimator and said entrance face, said diaphragm being adapted for passing through in a time one respective defined path of rays via the base face of said prism to one of said sample detection ranges, switching state of said diaphragm being adapted to be fed into an evaluation and control unit via a data and control line, said evaluation and control unit being for associating the actual switching state of said diaphragm to a respective spectrum corresponding to said actual switching state, spectra being obtainable by detection of the light leaving a prism exit face by way of a further collimator, an aperture of said further collimator being matched to said base face of said prism, an exit of said further collimator being connected to a further light conducting fiber, and the exit of said further light conducting fiber forming the entrance of a polychromator, within said polychromator the spectrally decomposed light being fed into a CCD-array and into a diode array, respectively, an exit of said CCD-array and diode array, respectively, being connected to said evaluation and control unit via a data-line.

2. An arrangement as claimed in claim 1, wherein the collimator and the further collimator, the optical prism and the locally multifold switchable diaphragm are in a fixed mutual relation and are integrated within a measuring head.

3. An arrangement as claimed in claim 1 or 2, wherein the locally multifold switchable diaphragm is so designed is that it has at least two slit-shaped aperture ranges that are adapted to be alternately set into an open or shut state, and the length of said slit-shaped aperture ranges are determined in such a way that an image thereof substantially covers the base face of the prism in one direction of extension.

4. Arrangement as claimed in claim 1 or 2, wherein a liquid crystal cell arranged between two optical polarizers is used for the locally multifold switchable diaphragm, said liquid crystal cell is adapted to set defined ranges into an open or shut state for the light passage by a respective design of electrodes.

5. Arrangement as claimed in claim 1 or 2, wherein the locally multifold switchable diaphragm is formed by a combination of a slit diaphragm and a rotatable multi-hole disk diaphragm that is rotatable and/or displaceable relative to said slit diaphragm.

6. Arrangement as claimed in claim 1, wherein the sample cell is formed by a receptacle which can be mounted on the base face of the prism, whereby an inner bottom of the receptacle is provided with the thin metal layer selected for SPR.

7. Arrangement as claimed in claim 6, wherein the cell has at least one immobilized sample detection, and in that at least one further sample detection range is kept free from an immobilized surface coverage and is used as reference channel.

8. Arrangement as claimed in claim 7, wherein the immobilized sample detection ranges are arranged separated and spaced from said sample detection range, which is kept free from an immobilized surface coverage, by a wall.

9. Arrangement as claimed in claim 7, wherein at least as one immobilized sample detection range is divided into a plurality differently immobilized ranges.

10. Arrangement as claimed in claim 1 or 7, wherein (n+1) slits in the diaphragm or in a unit operative as a diaphragm are provided at a number of n strip-shaped detectable immobilized sample detection ranges.

11. An arrangement for performing a surface plasmon resonance spectroscopy (SPR) method, comprising:

an optical prism, a sample cell being associated to said prism, said sample cell having at least two sample detection ranges;

a metal layer adapted for the SPR method provided for said sample cell and said optical prism;

at least one of said sample detection ranges being designed as a surface immobilized sample detection range, a light source for emitting light, a light conducting fiber and a collimator for directing said light to an entrance face of said optical prism, said collimator having an aperture adapted to a base face of said optical prism, a switchable diaphragm disposed between said collimator and said entrance face of said optical prism, an evaluation and control unit for controlling said switchable diaphragm, a further collimator for detecting light leaving a prism exit face of said optical prism, said further collimator having an aperture applied to said base face of said optical prism, a further light conducting fiber connected to an exit of said further collimator, a polychromator for receiving light from said light conducting fiber, a detector for receiving light from said polychromator, and said evaluation and control unit receiving and evaluating signals from said detector.

12. An arrangement as claimed in claim 11, wherein the collimator and the further collimator, the optical prism and the switchable diaphragm are in a fixed mutual relation and are integrated within a measuring head.

13. An arrangement as claimed in claim 11 or 12, wherein the switchable diaphragm has at least two slit-shaped aperture ranges that are adapted to be alternately set into an open or shut state, and a length of said slit-shaped aperture ranges is determined in such a way that an image thereof substantially covers the base face of the prism in one direction of extension.

14. Arrangement as claimed in claim 11 or 12, wherein said switchable diaphragm is a liquid crystal cell and two optical polarizers, and said liquid crystal cell is disposed between said two optical polarizers.

15. Arrangement as claimed in claim 11 or 12, wherein the switchable diaphragm is formed by a combination of a slit diaphragm and a rotatable multi-hole disk diaphragm that is displaceable relative to said slit diaphragm.

16. Arrangement as claimed in claim 11, wherein the sample cell is formed by a receptacle which is mounted on the base face of the prism, and an inner bottom of the receptacle is provided with the thin metal layer selected for SPR.

17. Arrangement as claimed in claim 16, further comprising said sample cell having at least one reference channel.

18. Arrangement as claimed in claim 17, further comprising a wall separating said immobilized sample detection range from said reference channel.

19. Arrangement as claimed in claim 17, wherein the at least as one immobilized sample detection range is divided into a plurality different immobilized ranges.

20. Arrangement as claimed in claim 11 or 17, wherein the switchable diaphragm has (n+1) slits and n number of said sample detection ranges.

* * * * *